US007018643B2

(12) United States Patent
Puterka et al.

(10) Patent No.: US 7,018,643 B2
(45) Date of Patent: Mar. 28, 2006

(54) PESTICIDE DELIVERY SYSTEM

(75) Inventors: Gary J. Puterka, Shepherdstown, WV (US); David Michael Glenn, Shepherdstown, WV (US); Dennis G. Sekutowski, Stockton, NJ (US)

(73) Assignees: Engelhard Corporation, Iselin, NJ (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/302,401

(22) Filed: Nov. 22, 2002

(65) Prior Publication Data

US 2003/0077309 A1     Apr. 24, 2003

Related U.S. Application Data

(62) Division of application No. 09/677,048, filed on Oct. 2, 2000, now Pat. No. 6,514,512.

(51) Int. Cl.
*A01N 25/32* (2006.01)

(52) U.S. Cl. .................. 424/406; 71/31; 71/64.07; 424/405; 424/407; 424/409; 424/421; 504/101; 504/113; 504/116.1

(58) Field of Classification Search ........ 424/400–407, 424/409–421; 71/31, 64.07, 64.08; 504/101, 504/113, 116.1
See application file for complete search history.

(56) References Cited

U.S. PATENT DOCUMENTS

| | | | | |
|---|---|---|---|---|
| 3,120,445 A | | 2/1964 | Aluisi et al. ................ 106/286 |
| 3,159,536 A | * | 12/1964 | Marotta ...................... 424/600 |
| 3,243,390 A | * | 3/1966 | Hillard et al. ................ 260/8 |
| 3,917,814 A | * | 11/1975 | Hedges et al. ............... 424/406 |
| 4,071,374 A | | 1/1978 | Minton ........................ 106/189 |
| 4,382,868 A | | 5/1983 | House .......................... 252/28 |
| 4,927,635 A | * | 5/1990 | Loschiavo ................... 424/409 |
| 5,151,122 A | | 9/1992 | Atsumi et al. ................ 106/35 |
| 5,180,420 A | | 1/1993 | Katayama et al. .......... 504/116 |
| 5,693,344 A | | 12/1997 | Knight et al. ............... 424/687 |
| 5,876,758 A | * | 3/1999 | Meybeck et al. ........... 427/490 |
| 5,997,945 A | | 12/1999 | Shasha et al. ............. 427/213.3 |
| 6,001,382 A | * | 12/1999 | Levy ............................ 424/405 |

FOREIGN PATENT DOCUMENTS

| | | | |
|---|---|---|---|
| WO | 9312761 | | 7/1993 |
| WO | 9409626 | | 5/1994 |
| WO | 98/38867 | * | 9/1998 |
| WO | 9838848 | | 9/1998 |
| WO | 9838855 | | 9/1998 |
| WO | 9838866 | | 9/1998 |
| WO | 0032046 | | 6/2000 |

OTHER PUBLICATIONS

Bar-Joseph, et al. "Spraying Citrus Plants with Kaolin Suspensions Reduces Colonization by the Spiraca Aphid (Aphis Citricola Van Der Goot)," *Crop Protection* (1983) 2 (3), 371-374.

Jack, et al. "The Effect Of Suspended Clay on Ciliate Population Growth Rates," *Freshwater Biology* (1993) 29, 385-394.

Melichar, et al. "Evaluation of Physical Insecticides," *Science Pharm. Proc.* 25th (1966), Meeting Date 1965, vol. 2, 589-97.

Yamamoto, N. "Insecticides in the Solid Form" *Jpn, Kokai Tokkyo Koho*, 10.

International Search Report dated May 7, 2002 related to PCT/US01/30703 filed Oct. 2, 2001.

* cited by examiner

*Primary Examiner*—Neil S. Levy
(74) *Attorney, Agent, or Firm*—Melanie L. Brown; Amin & Turocy, LLP

(57) ABSTRACT

In one embodiment, the present invention relates to a pesticide delivery system, containing a continuous film having a thickness from about 1 μm to about 1,000 μm and noncontinuous areas having sizes less than about 100 μm, the continuous film containing a particulate material wherein at least 90% by weight of the particulate material has a particle size of about 10 microns or less, and a pest control agent at least partially coating the particulate material. In another embodiment, the present invention relates to a method of delivering a pest control agent to a target organism, involving the steps of applying to at least a portion of a surface of a plant an effective amount of finely divided particulate material at least partially coated with the pest control agent, the particulate material containing from about 25% to about 100% by weight of a heat treated particulate material, wherein the partially coated finely divided particulate material as applied permits an exchange of gases on the surface of the plant and the partially coated finely divided particulate material forms a continuous film over the portion of the plant surface to which it is applied, and a maximum average size of openings in the continuous film is less than about 100 μm.

26 Claims, No Drawings

PESTICIDE DELIVERY SYSTEM

RELATED APPLICATIONS

This application is a divisional of co-pending application Ser. No. 09/677,048 filed Oct. 2, 2000, now U.S. Pat. No. 6,514,512.

FIELD OF THE INVENTION

The present invention is directed to a pesticide delivery system and improved methods for enhancing the activity of pesticides by improving delivery to target organisms.

BACKGROUND OF THE INVENTION

Pests, from microbial pests to insect pests, destroy inordinate amounts crops. Improved methods for protecting plants from pests are therefore desired since they would increase the amount and stability of food production. However, pesticides can be difficult to apply, and expensive to maintain after application. Applying toxicants as dry pesticides called dusts is not desirable because it leads to uncontrolled drifting of potentially dangerous chemicals. Applying toxicants in liquids as pesticidal sprays leads to less drifting than dust applications. Nevertheless, regardless of the formulation and application method, the efficacy of a toxicant primarily depends upon its delivery to the target organism.

Pesticidal sprays typically leave residues on plant surfaces. These residues represent an inefficient manner for contact with insects and other pests. Poor pesticide delivery leads to sub-lethal doses of pesticides. Often times, even with adequate spraying or delivery, residues from conventional pesticidal sprays delivered by a water carrier alone do not provide a proper (e.g., lethal) dose to an insect. Efficacy of a pesticidal residue on a plant surface requires that the residue remain on the surface long enough to contact a pest. Surfaces such as leaves, bark, soil, and wood may undesirably absorb pesticide residues and therefore lower the effectiveness thereof. In other words, pesticides loose their effectiveness when applied to sorptive surfaces since contact with pests is inhibited.

Moreover, pesticide application can result in reduced photosynthesis. Generally speaking, pesticide sprays cause a short-term and long-term reduction in the rate of $CO_2$ uptake (necessary for photosynthesis) and enhance leaf senescence. Thus, although plant survival may increase with a pesticide application, decreased transpiration and decreased photosynthesis undesirably occurs. Photosynthesis and transpiration in plants are positively linked in that a decrease in transpiration generally leads to a decrease in photosynthesis.

In perennial crop production such as tree fruit, flower buds for the subsequent year are initiated while fruit are developing for the current growing season. In practice, a plant may or may not produce flower buds for the subsequent year. One of the many biochemical cues to develop flower buds is the rate of photosynthesis and the availability of photosynthetically derived carbohydrates for flower bud development.

The availability of carbohydrates is limited by the photosynthetic capacity of the plant and the pool of carbohydrates is partitioned between the competing carbohydrate needs of the woody tissue, leaf tissue, developing flower buds and developing fruit. If photosynthesis is limited during the flower bud initiation period, flower bud initiation is reduced and fewer flowers are produced the following season. Reduced flower number results in reduced fruit number. In the subsequent year, the tree has a reduced number of fruit and it develops excessive numbers of flower buds because it lacks the competing developing fruit when flower buds are initiated. The alternating production of large and small numbers of fruit is an undesirable condition known as "alternate bearing".

A related problem to alternate bearing is called "excessive fruit drop". Normal fruit drop occurs when, simultaneously, the fruit is developing, tree growth is occurring, and flower buds are being initiated. Photosynthetically derived carbohydrates become limiting to all the growing tissues at this time in the growing season and the plant aborts the developing fruit, and limits the initiation of flower buds. When pesticide application deleteriously effects or diminishes photosynthesis, fruit drop is excessive.

Particle carriers for pesticides are generally suitable for control of soil-borne pests. They are not frequently used for foliar control of insects on plants due to difficulties associated with sticking to the foliage, impeding photosynthesis, and/or consequent susceptibility to removal by wind, rain, or other disturbing forces. Particle carriers for plant protection are not necessarily efficient or economic in view of these difficulties.

SUMMARY OF THE INVENTION

The present invention provides a pesticide delivery system and improved methods of delivering pesticides to target organisms. The present invention provides methods of increasing the amount and/or effectiveness of a pesticide or other pest control agent delivered to a target organism compared to conventional methods. The present invention also provides methods of delivering a pest control agent to a plant and simultaneously increasing the photosynthesis (or at least not diminishing the photosynthesis of the plant).

In one embodiment, the present invention relates to a pesticide delivery system, containing a continuous film having a thickness from about 1 µm to about 1,000 µm and noncontinuous areas having sizes less than about 100 µm, the continuous film containing a particulate material wherein at least 90% by weight of the particulate material has a particle size of about 10 microns or less, and a pest control agent at least partially coating the particulate material.

In another embodiment, the present invention relates to a method of delivering a pest control agent to a target organism, involving the steps of applying to at least a portion of a surface of a plant an effective amount of finely divided particulate material at least partially coated with the pest control agent, the particulate material containing from about 25% to about 100% by weight of a heat treated particulate material, wherein the partially coated finely divided particulate material as applied permits an exchange of gases on the surface of the plant and the partially coated finely divided particulate material forms a continuous film over the portion of the plant surface to which it is applied, and a maximum average size of openings in the continuous film is less than about 100 µm.

In yet another embodiment, the present invention relates to a method for making a pest control film, involving the steps of combining a volatile liquid, a pest control agent, and a particulate material wherein at least 90% by weight of the particulate material has a particle size of about 5 microns or less to form a slurry; applying the slurry to a substrate; and permitting at least a portion of the volatile liquid of the slurry to evaporate thereby forming the pest control film comprising pest control agent coated particulate material on the substrate, the pest control film containing from about 0.01% to about 10% by weight of the pest control agent and from about 90% to about 99.99% by weight of the particulate material, wherein the pest control film permits an exchange of gases between a horticultural substrate and the environment.

DETAILED DESCRIPTION OF THE INVENTION

This invention relates to pesticide delivery systems and methods of delivering pest control agents to target organisms. The methods may involve applying particulate materials containing at least one pest control agent, which may form a film, on a plant thereby increasing the effects of the pest control agent. The deleterious effects of pests on the plant are reduced or eliminated while photosynthesis is not diminished.

Photosynthesis is a process by which photosynthetic plants utilize solar energy to build carbohydrates and other organic molecules from carbon dioxide and water. The conversion of carbon dioxide to such organic molecules is generally referred to as carbon fixation or photosynthesis. The effects of enhanced photosynthesis are typically observed by increased yields/productivity, e.g., increased fruit size or production (usually measured in weight/acre), improved color, increased soluble solids, e.g. sugar, acidity, etc., and reduced plant temperature. Non-diminished photosynthesis is typically observed by little or no change in yields/productivity.

The substrates to which the present invention relates include horticultural crops such as actively growing agricultural crops, fruiting agricultural crops, actively growing ornamental crops, fruiting ornamental crops and the products thereof, and other surfaces pests infest such as manmade structures and stored grains/fruits/nuts/seeds. Specific examples include fruits, vegetables, trees, flowers, grasses, and landscape plants and ornamental plants. Particularly preferred plants include apple trees, pear treas, peach trees, plum trees, lemon trees, grapefruit trees, avocado trees, orange trees, apricot trees, walnut trees, raspberry plants, strawberry plants, blueberry plants, blackberry plants, bosenberry plants, corn, beans including soybeans, squash, tobacco, roses, violets, tulips, tomato plants, grape vines, pepper plants, wheat, barley, oats, rye, triticale, and hops. Man-made structures include buildings, storage containers, dwellings made of various materials such as plastics, wood, stone, cement, and metal.

The pesticide delivery systems of the present invention contain at least one particulate material and at least one pest control agent. The pest control agent at least partially coats the outside of the particulate material. In another embodiment, the pest control agent substantially coats the outside of the particulate material. In yet another embodiment, the pest control agent completely coats the outside of the particulate material.

While not wishing to be bound by any theory, it is believed that since the particulate material readily adheres to target organisms, and since the pest control agent at least partially coats the particulate material forming a continuous matrix, a relatively large amount of pest control agent is delivered to the target organism.

For purposes of this invention, pest control agents are compounds that effect the behavior or mortality of a target organism, such as a pesticide. Pest control agents include pesticides, insecticides, acaracides, fungicides, bactericides, herbicides, antibiotics, antimicrobials, nemacides, rodenticides, entomopathogens, phermones, attractants, plant growth regulators, insect growth regulators, chemosterilants, microbial pest control agents, repellents, viruses, phagostimulents, and plant nutrients. Plant nutrients include nitrogen, magnesium, calcium, boron, potassium, copper, iron, phosphorus, manganese, and zinc. Specific examples of these pesticides are known to those skilled in the art, and many are readily commercially available.

Target organisms are susceptible to behavior modification and/or physical debilitation due to exposure to a pesticide or pest control agent. Target organisms range from bacteria to arthropods to microbes to plants. For example, target organisms include bacteria, fungus, worms including nematodes, insects, arachnids such as spiders and mites, birds, rodents, deer, rabbit, and undesirable vegetation (weeds).

In some embodiments, two or more pest control agents are employed in the pesticide delivery systems of the present invention. For example, a pesticide delivery system may contain an insecticide and a phermone or other attractant. In this instance, an attract and kill mechanism is employed. The pest control agent partially, substantially or entirely coats the outside of the particulate material. In other words, the pest control agent need not entirely coat the outside of the particulate material. In some instances, it is preferable that the pest control agent partially coat the outside of the particulate material, as the exposed regions of the particulate material may enhance secure attachment to a target organism. In other instances, it is preferable that the pest control agent substantially or entirely coat the outside of the particulate material, as the pest control agent, especially in the case of an oil based pesticide, securely attach to a target organism.

In one embodiment, the particulate materials suitable for use in the present invention are highly reflective. As used herein, "highly reflective" means a material having a "Block Brightness" of at least about 80 and preferably at least about 90 and more preferably at least about 95 as measured by TAPPI standard T 452. Measurements can be made on a Reflectance Meter Technidyne S-4 Brightness Tester manufactured by Technidyne Corporation which is calibrated at intervals not greater than 60 days using brightness standards (paper tabs and opal glass standards) supplied by the Institute of Paper Science or Technidyne Corporation. Typically a particle block or plaque is prepared from 12 grams of a dry (<1% free moisture) powder. The sample is loosely placed in a cylinder holder and a plunger is slowly lowered over the sample to a pressure of 29.5–30.5 psi and held for about 5 seconds. The pressure is released and the plaque is examined for defects. A total of three plaques are prepared and three brightness values are recorded on each plaque by rotating the plaque about 120 degrees between readings. The nine values are than averaged and reported.

In one embodiment, the particulate materials suitable for use in the present invention are heat treated particulate materials. For purposes of this invention, heat treated particulate materials are particulate materials that are heated to an elevated temperature and include baked particulate materials, dehydrated particulate materials, calcined particulate materials, and fired particulate materials. Heat treated particulate materials may be hydrophobic. Specific examples include calcined calcium carbonate, calcined talc, calcined kaolin, baked kaolin, fired kaolin, metakaolin, calcined bentonites, calcined clays, calcined pyrophyllite, calcined silica, calcined feldspar, calcined sand, calcined quartz, calcined chalk, calcined limestone, calcined precipitated calcium carbonate, baked calcium carbonate, calcined diatomaceous earth, calcined barytes, calcined aluminum trihydrate, calcined pyrogenic silica, calcined titanium dioxide dehydrated kaolin, dehydrated calcium carbonate, dehydrated bentonites, and dehydrated limestone.

Heat treatment in accordance with the invention involves heating a particulate material at a temperature from about 300° C. to about 1,200° C. for about 10 seconds to about 24 hours. In a preferred embodiment, heat treatment involves heating a particulate material at a temperature from about 400° C. to about 1,100° C. for about 1 minute to about 15 hours. In a more preferred embodiment, heat treatment involves heating a particulate material at a temperature from about 500° C. to about 1,000° C. for about 10 minutes to about 10 hours. The heat treatment may be carried out in air, in an inert atmosphere or under a vacuum.

In most embodiments, the particulate materials contain at least about 25% by weight, and particularly about 25% to about 100% by weight of heat treated particulate materials. In another embodiment, the particulate materials contain at least about 40% by weight, and particularly about 40% to about 99% by weight of heat treated particulate materials. In yet another embodiment, the particulate materials contain at least about 60% by weight, and particularly about 60% to about 95% by weight of heat treated particulate materials. In still yet another embodiment, the particulate materials contain at least about 70% by weight, and particularly about 70% to about 90% by weight of heat treated particulate materials.

In one embodiment, the heat treated particulate material comprises a heat treated kaolin, such as a metakaolin and/or a calcined kaolin. In another embodiment, the heat treated particulate material comprises a hydrophobic treated heat treated kaolin. Examples of preferred heat treated particulate materials that are commercially available from Engelhard Corporation, Iselin, N.J. are the metakaolins sold under the trade designation MetaMax, the calcined kaolins sold under the trademark Satintone® and the siloxane treated calcined kaolins sold under the trade designations Surround™ and Translink®.

In one embodiment, the particulate material is hydrophobic. In another embodiment, the particulate material is hydrophilic. In yet another embodiment, the particulate material contains hydrophobic materials and hydrophilic materials.

In addition to the heat treated particulate materials, the particulate materials may optionally further include supplemental particulate materials such as hydrophilic or hydrophobic materials and the hydrophobic materials may be hydrophobic in and of themselves, e.g., mineral talc, or may be hydrophilic materials that are rendered hydrophobic by application of an outer coating of a suitable hydrophobic wetting agent (e.g., the particulate material has a hydrophilic core and a hydrophobic outer surface).

In one embodiment, the particulate materials contain about 1% to about 75% by weight of supplemental particulate materials. In another embodiment, the particulate materials contain about 5% to about 60% by weight of supplemental particulate materials. In yet another embodiment, the particulate materials contain about 10% to about 30% by weight of supplemental particulate materials.

Typical supplemental particulate hydrophilic materials suitable for use in the present invention include: minerals, such as calcium carbonate, talc, hydrous kaolins, bentonites, pyrophyllite, silica, feldspar, sand, quartz, chalk, limestone, precipitated calcium carbonate, diatomaceous earth and barytes; functional fillers such as aluminum trihydrate, pyrogenic silica, sulfur, and titanium dioxide.

The surfaces of hydrophobic supplemental or heat treated materials can be made hydrophobic by contact with hydrophobic wetting agents. Many industrial mineral applications, especially in organic systems such as plastic composites, films, organic coatings or rubbers, are dependent upon just such surface treatments to render the mineral surface hydrophobic; see, for example, Jesse Edenbaum, *Plastics Additives and Modifiers Handbook*, Van Nostrand Reinhold, New York, 1992, pages 497–500 which is incorporated herein by reference for teachings of such surface treatment materials and their application. So-called coupling agents such as fatty acids and silanes are commonly used to surface treat solid particles as fillers or additives targeted to these industries. Such hydrophobic agents are well known in the art and common examples include: organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystreneo or Industrene® products obtained from Witco Corporation or Emersol® products obtained from Henkel Corporation (stearic acid and stearate salts are particularly effective fatty acids and salts thereof for rendering a particle surface hydrophobic).

Examples of preferred supplemental particulate materials that are commercially available include calcium carbonate commercially available from English China Clay under the trademarks Atomite® and Supermite® and stearic acid treated ground calcium carbonates commercially available from English China Clay under the trademarks Supercoat® and Kotamite®.

In one embodiment, the particulate materials and/or pesticide delivery systems of the present invention do not include calcium hydroxide. In another embodiment, the particulate materials and/or pesticide delivery systems of the present invention do not include starch. In yet another embodiment, the particulate materials and/or pesticide delivery systems of the present invention do not include hydrous kaolin. In still yet another embodiment, the particulate materials and/or pesticide delivery systems of the present invention do not include silica.

The term "finely divided" when utilized herein with the term "particulate materials" means that the particulate materials have a median individual particle size below about 10 microns and preferably below about 3 microns and more preferably the median particle size is about 1 micron or less, and even more preferably the median particle size is about 0.5 microns or less.

Particle size and particle size distribution as used herein are measured with a Micromeritics Sedigraph 5100 Particle Size Analyzer. Measurements were recorded in deionized water for hydrophilic particles. Dispersions were prepared by weighing 4 grams of dry sample into a plastic beaker adding dispersant and diluting to the 80 ml mark with deionized water. The slurries were then stirred and set in an ultrasonic bath for 290 seconds. Typically, for calcined kaolin 0.5% tetrasodium pyrophosphate is used as a dispersant; with calcined calcium carbonate 1.0% Calgon T is used. Typical densities for the various powders are programmed into the sedigraph, e.g., 2.58 g/ml for kaolin. The sample cells are filled with the sample slurries and the X-rays are recorded and converted to particle size distribution curves by the Stokes equation. The median particle size is determined at the 50% level.

In one embodiment, the particulate material has a particle size distribution wherein at least 90% by weight of the particles have a particle size of under about 10 microns. In another embodiment, the particulate material has a particle size distribution wherein at least 90% by weight of the particles have a particle size of below about 3 microns. In a preferred embodiment, the particulate material has a particle size distribution wherein at least 90% by weight of the particles have a particle size of about one micron or less. In still yet another embodiment, the particulate material has a particle size distribution wherein at least 90% by weight of the particles have a particle size of below about 0.5 microns. In this connection, the particulate material according to the present invention has a relatively narrow particle size distribution.

The particulate materials particularly suitable for use in this invention are inert and have low toxicity. As used herein, "inert" particulate materials are particles that are not phytotoxic. The particulate materials preferably have extremely low toxicity meaning that in the quantities needed for effective enhanced horticultural effects, the particulate materials are not considered harmful to animals, the environment, the applicator and the ultimate consumer. However, the pest control agent may or may not be characterized as inert and having low toxicity. Thus, while the particulate materials may be inert, the pesticide delivery system may or may not be characterized as inert and having low toxicity. Also as used herein, "inert" particulate materials are particles that do not decompose the pest control agent.

The present invention further relates to treated substrates such as horticultural crops wherein the surface of the plant is treated with the pesticide delivery system containing one or more particulate materials. This treatment should not materially affect the exchange of gases on the surface of the plant. The gases which pass through the pesticide delivery system treatment are those which are typically exchanged through the surface skin of living plants. Such gases typically include water vapor, carbon dioxide, oxygen, nitrogen and volatile organics.

The surface of a plant, such as a horticultural crop, is treated with an amount of the pesticide delivery system containing one or more highly reflective, finely divided particulate materials and one or more pest control agents that is effective in reducing or eliminating a target organism without diminishing photosynthesis of the plant. The extent of treatment coverage of a plant can be determined by one skilled in the art. Full coverage is preferred. Full coverage of areas where contact with the target organism is likely is also preferred. Less than full plant coverage is within the scope of this invention and can be highly effective, for example, neither the under surface of the plant (that which is not frequently contacted by some target organisms) need be treated by the method of this invention nor must the upper surface of the plant be completely covered; although full or substantially full plant substrate coverage is preferred. Particularly, full or substantially full fruit (or area where protection is desired) coverage is preferred, as other areas of a plant do not require such treatment. Full or substantially full plant substrate coverage can provide additional benefits such as effective disease control, smoother fruit surface, reduced bark and fruit cracking, and reduced russeting. The method of the present invention may result in a residue of the treatment forming a membrane of one or more layers of the pesticide delivery system containing the highly reflective particulate materials and pesticide on the plant surface.

The pesticide delivery system suitable for use in the present invention may be applied as a slurry of finely divided particulate materials in one or more volatile liquids such as water, a low boiling organic solvent or low boiling organic solvent/water mixture. In a preferred embodiment, the pest control agent is at least partially soluble in the volatile liquid.

The low boiling organic liquids useful in the present invention are preferably water-miscible and contain from 1 to about 6 carbon atoms. The term "low boiling" as used herein shall mean organic liquids which have a boiling point generally no more than about 100° C. These liquids contribute to the ability of the pesticide delivery system to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred low boiling organic liquid.

Low boiling organic liquids may be employed in applying the pesticide delivery system to plant substrates for the purposes of this invention. Typically, the liquids are used in an amount sufficient to form a dispersion of the pesticide delivery system. The amount of low boiling organic liquid is typically up to about 30 volume percent of the dispersion, preferably from about 1 to about 20 volume percent, preferably from about 3 to about 5 volume percent, and most preferably from about 3.5 to about 4.5 volume percent. The pesticide delivery system is preferably added to a low boiling organic liquid to form a slurry and then this slurry is diluted with water to form an aqueous dispersion. The resulting slurry retains the pesticide delivery system in finely divided form.

In one embodiment, the slurry contains from about 0.5% to about 50% by weight solids (particulate materials), less than about 5% by weight pest control agent, and from about 70% to about 99.5% by weight of a volatile liquid. In another embodiment, the slurry contains from about 1% to about 25% by weight solids (particulate materials), less than about 2% by weight pest control agent, and from about 75% to about 99% by weight of a volatile liquid. In yet another embodiment, the slurry contains from about 2% to about 15% by weight solids (particulate materials), less than about 1% by weight pest control agent, and from about 85% to about 98% by weight of a volatile liquid.

Adjuvants such as surfactants, dispersants, speaders/stickers (adhesives), wetting agents, antifoaming agents, and/or drift reducing agents may be incorporated in preparing an aqueous slurry of the pesticide delivery system of this invention. In one embodiment, the slurry of the pesticide delivery system consists essentially of the particulate materials, one or more pest control agents, and water and optionally at least one of supplemental particulate materials, low boiling organic solvents, surfactants, dispersants, spreaders/stickers, wetting agents, antifoaming agents, and drift reducing agents.

Surfactants and dispersants include nonionic surfactants, anionic surfactants, cationic surfactants and/or amphoteric surfactants and promote the ability of the aggregates to remain in solution during spraying (contribute to a better quality slurry). Surfactants and dispersants also function to break-up agglomerates of particulate materials.

Spreaders/stickers promote the ability of the pesticide delivery system to adhere to plant surfaces. Wetting agents reduce surface tension of water in the slurry and thus increase the surface area over which a given amount of the slurry may be applied. Antifoaming agents decreases foaming during spraying. Drift reducing agents prevent droplets from becoming too small thus reducing the ability of slurry droplets to drift during spraying.

One or more layers of the slurry can be sprayed or otherwise applied to the plant surface. The volatile liquid is preferably allowed to evaporate between coatings. The residue of this treatment may be hydrophilic or hydrophobic. Applying particles as a dust or brushing, although not being commercially practical on a large scale due to drift, inhalation hazards and poor residuality, is an alternative for carrying out the method of this invention. Spraying is a preferred method of application.

Spreader/stickers that can be mixed with hydrophilic particles (0.5% or more solids in water) to aid in spraying uniform treatments on a plant or horticultural substrate are, for example, modified phthalic glycerol alkyd resins such as Latron B-1956 from Rohm & Haas Co.; plant oil based materials (cocodithalymide) with emulsifiers; polymeric terpenes; nonionic detergents (ethoxylated tall oil fatty acids); guar gum; xanthane gum, latex, agar, starch, and the like.

In another embodiment, the amount of adjuvants in the aqueous slurry of the pesticide delivery system is from about 0.001% by weight to about 20% by weight. In yet another embodiment, the amount of adjuvants in the aqueous slurry of the pesticide delivery system is from about 0.01% by weight to about 10% by weight. In still yet another embodiment, the amount of adjuvants in the aqueous slurry of the pesticide delivery system is from about 0.1% by weight to about 5% by weight.

The pesticide treatment may be applied as one or more layers of a matrix of finely divided particulate materials/pest control agent. The amount of material applied is within the skill of one of ordinary skill in the art. The amount will be sufficient to protect plants, structures, and grains from target organism pests, and in the case of plants, without diminishing photosynthesis of the plant to which these particles are applied. For example, this can be accomplished by applying from about 25 up to about 5000 micrograms of pesticide delivery system/cm$^2$ of plant surface for particulate materials having specific density of around 2–3 g/cm$^3$, more typically from about 100 up to about 3000 micrograms of pesticide delivery system/cm$^2$ of plant surface for particulate materials having specific density of around 2–3 g/cm$^3$, and preferably from about 100 up to about 500 micrograms of pesticide delivery system/cm$^2$ of plant surface for particulate materials having specific density of around 2–3 g/cm$^3$. In addition, environmental conditions such as wind and rain may reduce plant coverage of the pesticide delivery system and therefore it is within the scope of this invention to apply the pesticide delivery system one or more times during the growing season of said horticultural plant so as to maintain the desired effect of invention.

After the slurry is applied to a substrate, the slurry is permitted to dry (the volatile liquids evaporate) wherein a continuous or substantially continuous film of the particulate materials is formed. By continuous, it is meant that, where applied, the dry film is continuous (or substantially continuous). For example, in an embodiment where the upper third of a fruit is covered with particulate material in accordance with the present invention, the film covering the upper third of the fruit is continuous or substantially continuous while the bottom two-thirds of the fruit is not covered with the particulate material.

Of the covered portion of a substrate surface, the pesticide delivery film is continuous in that it covers from about 75% to about 100% of the surface area, thus the openings or noncontinuous areas the pesticide delivery film constitutes from about 0% to about 25% of the surface area. In another embodiment, the pesticide delivery film is continuous in that it covers from about 90% to about 99.9% of the surface area, thus the openings or noncontinuous areas the pesticide delivery film constitutes from about 0.1% to about 10% of the surface area. In yet another embodiment, the pesticide delivery film is continuous in that it covers from about 95% to about 99% of the surface area, thus the openings or noncontinuous areas the pesticide delivery film constitutes from about 5% to about 1% of the surface area.

In the continuous film, the maximum average size (average diameter) of pores or noncontinuous areas in the pesticide delivery film is generally less than about 100 μm. In another embodiment, the maximum average size of openings or noncontinuous areas in the pesticide delivery film is generally less than about 10 μm. In yet another embodiment, the maximum average size of openings or noncontinuous areas in the pesticide delivery film is generally less than about 5 μm.

The thickness of the pesticide delivery film applied using a slurry ranges from about 1 μm to about 1,000 μm. In another embodiment, the thickness of the pesticide delivery film ranges from about 3 μm to about 750 μm. In yet another embodiment, the thickness of the pesticide delivery film ranges from about 5 μm to about 500 μm.

In one embodiment, the pesticide delivery film contains from about 0.01% to about 30% by weight of a pest control agent and from about 70% to about 99.99% by weight of a particulate material at least partially coated by the pest control agent. In another embodiment, the pesticide delivery film contains from about 0.05% to about 10% by weight of a pest control agent and from about 90% to about 99.95% by weight of a particulate material. In yet another embodiment, the pesticide delivery film contains from about 0.1% to about 5% by weight of a pest control agent and from about 95% to about 99.9% by weight of a particulate material.

The amount of the pesticide delivery system applied varies depending upon a number of factors including the manner of application, the identity of the substrate, the amount of plants per acre and the concentration of the particulate material and pest control agent in the slurry. Typically, the use rate of the pesticide delivery system applied is from about 10 gallons/acre to about 1,000 gallons per acre (where the concentration of the particulate material/pest control agent in the slurry is about 6% by weight solids).

Although continuous, the pesticide delivery film permits the exchange of gases (water and carbon dioxide transpiration and photosynthesis, respectively) on the portions of the surface of a plant to which it is applied. In this connection, the continuous pesticide delivery film is gas permeable or porous, but not discontinuous.

Moreover, since the target organism is partially covered in a matrix of the pesticide delivery film of the present invention, grooming and ingestion by the target organism either spreads the pest control agent over the surface of the organism (thereby maximizing contact area), or introduces the pest control agent into the internal organs/system of the pest. Both of these pathways enhance the behavior or mortality of the target organism by the pest control agent. Since the pesticide delivery system of the present invention effectively sticks to target organisms, a previously ineffective dosage of pest control agent (not used with the particulate materials of the present invention) becomes an effective lethal dose as the same amount of pest control agent is more efficiently used by the present invention compared to conventional systems/methods.

The pesticide delivery film formed in accordance with the present invention effectively blocks (absorbs, scatters and/or reflects away) excessive UV and/or IR radiation that has damaging effects on plant tissue and the pest control agent. In one embodiment, the pesticide delivery film formed in accordance with the present invention blocks (absorbs, scatters and/or reflects away) from about 1% to about 10% of the UV and/or IR radiation to which it is exposed. In another embodiment, the pesticide delivery film formed in accordance with the present invention blocks from about 2% to about 5% of the UV and/or IR radiation to which it is exposed. As a result, the photosynthetic and biochemical mechanisms of plants are not damaged or impeded by UV and/or IR radiation. The present invention in this embodiment provides a method that reduces UV and/or IR radiation at the plant surface that in turn reduces the environmental stress and increases photosynthesis. In many instances, reductions in UV and/or IR radiation reduces the degradation of a pest control agent; thus, the pesticide delivery system of the present invention extends the effectiveness or enhances the effects of a pest control agent over a longer period of time.

The pesticide delivery film formed in accordance with the present invention can be readily and easily removed from substrates which are so treated. In one embodiment, the pesticide delivery film can be and easily removed from treated surfaces using a high pressure water sprayer, wherein the water contains or does not contain a suitable surfactant. The identity of the surfactant depends upon the specific identity of the pesticide delivery system, whether or not any adjuvants are present, and the amount of any adjuvant, if any. In another embodiment, the pesticide delivery film can be and easily removed from plants or fruits using a water bath or water spray, wherein the water contains or does not contain a suitable surfactant, and optionally brushing the plant or fruit.

Although the pesticide delivery system can be applied over plants, the system does not materially effect, and in most instances, does not diminish the photosynthesis of the plants. In other words, contrary to conventional pesticide treatments that attempt to reduce populations of target organisms while undesirably diminishing photosynthesis, the present invention provides a pesticide delivery system that is applied over plants to reduce populations of target organisms while not diminishing photosynthesis. In one embodiment, application of the pesticide delivery system in accordance with the present invention enhances the photosynthesis of the treated plants.

The following examples illustrate the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

The enhanced effect of reducing fireblight in apple trees with the pesticide delivery system of the present invention containing bactericides is examined and compared to conventional pesticides.

Experiments are conducted on potted trees of 'Rome' apple in a naturally illuminated greenhouse. When about 80% of the blooms are open, open blossoms are sprayed to drip with 108 CFU of *Erwinia amylovora* (Ea) strain AFRS-581. After drying for about 1 hour, each the following treatments are applied to six of the infected trees. Slurries containing particulate materials (PM) (3% weight by volume), water and copper hydroxide at 0.5 g/l (Copper Count N from Mineral Research Development Co., Charlotte, N.C., a bactericide), Blight Ban at 1 g/l (from Plant Health Technologies, Boise, Id., a microbial bactericide), or streptomycin at 0.5 g/l (from Novartis Crop Protection Inc., Greensboro, N.C., an antibiotic); and slurries containing PM (3% weight by volume) and water; and mixtures of water and copper hydroxide at 0.5 g/l, Blight Ban at 1 g/l, or streptomycin at 0.5 g/l are applied to the apple trees. In Example 1 and Example 2 (below), the particulate material is Surround™ WP available from Engelhard Corporation, Iselin, N.J., which is a calcined kaolin with an organic spreader/sticker.

After 7 days, blossom necrosis symptoms are present and recorded. Disease data are expressed as percentage of blossom infect rate. Table 1 lists the data.

TABLE 1

| Treatment | % Blossom Infection |
| --- | --- |
| PM | 71.1 |
| copper hydroxide | 87.1 |
| Blight Ban | 82.4 |
| streptomycin | 83.3 |
| PM/copper hydroxide | 60.2 |
| PM/Blight Ban | 46.3 |
| PM/streptomycin | 44.2 |

EXAMPLE 2

The enhanced activity of insecticides against pear psylla in 'Sekel' pear trees applied with the pesticide delivery system of the present invention is examined and compared to conventional insecticides.

Four 'Sekel' pear trees infested with pear psylla nymphs are each treated with PM (3% weight by volume) and water; PM (3% weight by volume), water, and Dimilin at 4 oz AI/a and 8 oz AI/a (an insect growth regulator) (Active Ingredient per acre); PM (3% weight by volume), water, and Agri-Mek at 2.5 oz AI/a and 5 oz AI/a (a neurotoxin insecticide); water and Dimilin at 4 oz AI/a and 8 oz AI/a; water and Agri-Mek at 2.5 oz AI/a and 5 oz AI/a; or untreated. Four infested leaves are taken from each treatment of each tree to assess live and dead psylla nymphs before treatments are applied and 14 days after treatment. The % mortality is reported in Table 2.

TABLE 2

| Treatment | % Mortality |
| --- | --- |
| untreated | 5 |
| PM | 33 |
| A-M-2.5 | 31 |
| A-M-5 | 28 |
| Dimilin-4 | 45 |
| Dimilin-8 | 26 |
| PM/A-M-2.5 | 32 |
| PM/A-M-5 | 50 |
| PM/Dimilin-4 | 62 |
| PM/Dimilin-8 | 68 |

Table 1 shows that the blossom infect rate of apple trees by *Erwinia amylovora* is markedly lower when a pesticide delivery system in accordance with the present invention is employed. That is, when the bactericide, microbial bactericide, or antibiotic is combined with particulate material as described herein (in accordance with the present invention), the rates of infection is reduced compared using the bactericide, microbial bactericide, or antibiotic without particulate material. Table 2 shows similar results. In particular, Table 2 shows an increased mortality rate of nymphs on pear trees when using an insecticide combined with particulate material in accordance with the present invention compared to using the insecticide alone or without particulate material.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A pesticide delivery system, comprising:
    a continuous film having a thickness from about 1 μm to about 1,000 μm and noncontinuous areas having sizes less than about 100 μm, the continuous film comprising
        a particulate material wherein at least 90% by weight of the particulate material has a particle size of about 10 microns or less, the particulate material comprising from about 25% to about 100% of a heat treated particulate material selected from the group consisting of calcined calcium carbonate, calcined talc, calcined kaolin, metakaolin, calcined bentonites, calcined clays, calcined pyrophyllite, calcined feldspar, calcined chalk, calcined limestone, calcined precipitated calcium carbonate, calcined diatomaceous earth, calcined barytes, calcined aluminum trihydrate, and calcined titanium dioxide, the heat treated particulate material heated to a temperature from about 300° C. to about 1,200° C., the heat treated particulate material being highly reflective, and
        an effective amount of a pest control agent at least partially coating the particulate material to effect mortality of a pest, pest control agent comprising at least one elected from the group consisting of an insecticide, an acaracide, a fungicide, a bactericide, an antibiotic, an antimicrobial, a nemacide, a rodenticide, and an entomopathogen.

2. The pesticide delivery system of claim 1, wherein the particulate material is hydrophobic.

3. The pesticide delivery system of claim 1, wherein the particulate material comprises a heat treated particulate material heated to a temperature from about 400° C. to about 1,100° C.

4. The pesticide delivery system of claim 1, wherein the particulate material has a particle size distribution wherein at least 90% by weight of the particulate material have a particle size under about 3 microns.

5. The pesticide delivery system of claim 1, wherein the particulate material comprises a hydrophilic core and a hydrophobic outer surface.

6. The pesticide delivery system of claim 1, wherein the continuous film comprises from about 0.01% to about 30% by weight of the pest control agent and from about 70% to about 99.99% by weight of the particulate material.

7. The pesticide delivery system of claim 1, wherein the particulate material comprises one or more of calcined calcium carbonate, calcined kaolin, metakaolin, and calcined bentonites.

8. The pesticide delivery system of claim 5, wherein said hydrophobic outer surface materials are selected from the group consisting of organic titanates, organic zirconate or aluminate coupling agents, organofunctional silanes, modified silicone fluids and fatty acids and salts thereof.

9. The pesticide delivery system of claim 1, wherein the continuous film further comprises at least one of a surfactant, a dispersant, a spreader/sticker, a wetting agent, an antifoaming agent, and a drift reducing agent.

10. The pesticide delivery system of claim 1, wherein the particulate material comprises from about 40% to about 99% by weight of a heat treated particulate material.

11. A pesticide delivery system, comprising:
    a particulate film permitting an exchange of gases on a substrate surface to which it is applied, comprising
        a particulate material comprising from about 25% to about 100% by weight of a heat treated particulate material, wherein at least 90% by weight of the particulate material has a particle size of about 10 microns or less, the heat treated particulate material selected from the group consisting of calcined calcium carbonate, calcined talc, calcined kaolin, metakaolin, calcined bentonites, calcined clays, calcined pyrophyllite, calcined feldspar, calcined chalk, calcined limestone, calcined precipitated calcium carbonate, calcined diatomaceous earth, calcined barytes, calcined aluminum trihydrate, and calcined titanium dioxide, the heat treated particulate material heated to a temperature from about 300° C. to about 1,200° C., the heat treated particulate material being highly reflective, and
        an effective amount of a pest control agent at least partially coating the particulate material to effect mortality of a pest, pest control agent comprising at least one elected from the group consisting of an insecticide, an acaracide, a fungicide, a bactericide, an antibiotic, an antimicrobial, a nemacide, a rodenticide, and an entomopathogen.

12. The pesticide delivery system of claim 11, wherein the particulate film has a thickness from about 1 μm to about 1,000 μm.

13. The pesticide delivery system of claim 11, wherein the particulate material comprises calcined kaolin.

14. The pesticide delivery system of claim 11, wherein at least 90% by weight of the particulate material has a particle size under about 3 microns.

15. The pesticide delivery system of claim 11, wherein the pest control agent comprises at least one of an insecticide, an acaracide, a fungicide, and a bactericide.

16. The pesticide delivery system of claim 11, wherein the particulate material further comprises at least one of calcium carbonate, talc, hydrous kaolin, bentonites, clays, pyrophyllite, silica, feldspar, sand, quartz, chalk, limestone, precipitated calcium carbonate, diatomaceous earth, barytes, aluminum trihydrate, pyrogenic silica, and titanium dioxide.

17. The pesticide delivery system of claim 11, wherein at least one of a surfactant, a dispersant, a spreader/sticker, a wetting agent, and a drift reducing agent is combined with the pest control agent and the particulate material.

18. The pesticide delivery system of claim 11, wherein the particulate material comprises a heat treated particulate material heated to a temperature from about 400° C. to about 1,200° C.

19. The pesticide delivery system of claim 11, wherein the film comprises from about 0.01% to about 30% by weight of the pest control agent and from about 70% to about 99.99% by weight of the particulate material.

20. The pesticide delivery system of claim 1, wherein the pest control agent further comprises at least one plant nutrient selected from the group consisting of nitrogen, magnesium, boron, potassium, copper, iron, phosphorus, manganese, and zinc.

21. The pesticide delivery system of claim 11, wherein the pest control agent further comprises at least one plant nutrient selected from the group consisting of nitrogen, magnesium, boron, potassium, copper, iron, phosphorus, manganese, and zinc.

22. A pesticide delivery system, comprising:
a continuous film on a plant having a thickness from about 1 μm to about 1,000 μm and noncontinuous areas having sizes less than about 100 μm, the continuous film comprising
a particulate material wherein at least 90% by weight of the particulate material has a particle size of about 10 microns or less, the particulate material comprising from about 25% to about 100% of a heat treated particulate material selected from the group consisting of calcined calcium carbonate, calcined talc, calcined kaolin, metakaolin, calcined bentonites, calcined clays, calcined pyrophyllite, calcined feldspar, calcined chalk, calcined limestone, calcined precipitated calcium carbonate, calcined diatomaceous earth, calcined barytes, calcined aluminum trihydrate, and calcined titanium dioxide, the heat treated particulate material heated to a temperature from about 300° C. to about 1,200° C., the heat treated particulate material being highly reflective, and
an effective amount of a pest control agent at least partially coating the particulate material to enhance photosynthesis of the plant, the pest control agent comprising at least one plant nutrient selected from the group consisting of nitrogen, magnesium, boron, potassium, copper, iron, phosphorus, manganese, and zinc.

23. The pesticide delivery system of claim 22, wherein the pest control agent further comprises at least one of an insecticide, an acaracide, a fungicide, a bactericide, a herbicide, an antibiotic, an antimicrobial, a nemacide, a rodenticide, an entomopathogen, a phermone, a chemosterilant, a virus, an attractant, a plant growth regulator, an insect growth regulator, a repellent, and a phagostimulent.

24. The pesticide delivery system of claim 22, wherein the particulate material comprises one or more of calcined calcium carbonate, calcined kaolin, metakaolin, and calcined bentonites.

25. The pesticide delivery system of claim 22, wherein the continuous film comprises from about 0.01% to about 30% by weight of the pest control agent and from about 70% to about 99.99% by weight of the particulate material.

26. The pesticide delivery system of claim 22, wherein at least one of a surfactant, a dispersant, a spreader/sticker, a wetting agent, and a drift reducing agent is combined with the pest control agent and the particulate material.

* * * * *